United States Patent
Kalgaonkar et al.

(10) Patent No.: US 11,203,712 B1
(45) Date of Patent: Dec. 21, 2021

(54) METHODS AND COMPOSITIONS OF USING VISCOELASTIC SURFACTANTS AS DIVERSION AGENTS

(71) Applicants: SAUDI ARABIAN OIL COMPANY, Dhahran (SA); KING FAHD UNIVERSITY OF PETROLEUM & MINERALS, Dhahran (SA)

(72) Inventors: Rajendra Arunkumar Kalgaonkar, Dhahran (SA); Khalid Alnoaimi, Aberdeen (GB); Nour Baqader, Khobar (SA); Nisar Ullah, Dhahran (SA); Muhammed Mansha, Dhahran (SA)

(73) Assignees: SAUDI ARABIAN OIL COMPANY, Dhahran (SA); KING FAHD UNIVERSITY OF PETROLEUM & MINERALS, Dhahran (SA)

( * ) Notice: Subject to any disclaimer, the term of this patent is extended or adjusted under 35 U.S.C. 154(b) by 0 days.

(21) Appl. No.: 16/895,752

(22) Filed: Jun. 8, 2020

(51) Int. Cl.
*C07C 33/04* (2006.01)
*C09K 8/584* (2006.01)
(Continued)

(52) U.S. Cl.
CPC .............. *C09K 8/604* (2013.01); *C07C 33/04* (2013.01); *C09K 8/584* (2013.01); *C09K 8/74* (2013.01);
(Continued)

(58) Field of Classification Search
None
See application file for complete search history.

(56) References Cited

U.S. PATENT DOCUMENTS 4,569,750 A * 2/1986 Brownawell ............ C10G 9/16
208/48 AA
5,250,642 A 10/1993 Ahmed et al.
(Continued)

FOREIGN PATENT DOCUMENTS

CN 104140802 A 11/2014
WO 2007056284 A2 5/2007
(Continued)

OTHER PUBLICATIONS

National Center for Biotechnology Information (2021). PubChem Compound Summary for CID 59566317, N-[3-(Dimethylamino) propyl]nonadecanamide. Retrieved Aug. 26, 2021 from https://pubchem.ncbi.nlm.nih.gov/compound/N-_3-_ Dimethylamino_ propyl_nonadecanamide. (Year: 2021).*

(Continued)

*Primary Examiner* — Charles R Nold
(74) *Attorney, Agent, or Firm* — Osha Bergman Watanabe & Burton LLP

(57) ABSTRACT

A wellbore fluid may include a gemini surfactant, a zwitterionic surfactant, an activator, and an aqueous base fluid. The gemini surfactant may have a structure represented by formula (I):

(Continued)

where $R^1$ is a $C_1$-$C_{10}$ hydrocarbon group, m and o are each, independently, an integer ranging from 1 to 4, and n is an integer ranging from 8 to 12.

30 Claims, 4 Drawing Sheets

(51) Int. Cl.
  *C09K 8/74* (2006.01)
  *E21B 43/27* (2006.01)
  *C09K 8/60* (2006.01)
  *E21B 43/16* (2006.01)

(52) U.S. Cl.
  CPC ...... *C09K 2208/06* (2013.01); *C09K 2208/30* (2013.01); *E21B 43/162* (2013.01)

(56) References Cited

U.S. PATENT DOCUMENTS

| | | | |
|---|---|---|---|
| 7,237,608 | B2 | 7/2007 | Fu et al. |
| 7,621,334 | B2 | 11/2009 | Welton et al. |
| 8,637,622 | B2 | 1/2014 | Monin et al. |
| 9,023,966 | B2 | 5/2015 | Zhang et al. |
| 9,080,095 | B2 | 7/2015 | Morvan et al. |
| 10,479,762 | B1 | 11/2019 | Hussain et al. |
| 2008/0045420 | A1 | 2/2008 | Karagianni et al. |
| 2011/0071056 | A1 | 3/2011 | Saini et al. |
| 2011/0224124 | A1* | 9/2011 | Fernandez Prieto ........ C11D 17/003 510/405 |
| 2012/0085534 | A1 | 4/2012 | Morvan et al. |
| 2013/0065813 | A1* | 3/2013 | Miravet Celades . C11D 7/3263 510/516 |
| 2019/0256458 | A1 | 8/2019 | Hussain et al. |

FOREIGN PATENT DOCUMENTS

| | | |
|---|---|---|
| WO | 2015/126418 A1 | 8/2015 |
| WO | 2018/213627 A1 | 11/2018 |

OTHER PUBLICATIONS

Hussain, S.M.S. et al.; "Synthesis of Novel Ethoxylated Quaternary Ammonium Gemini Surfactants for Enhanced Oil Recovery Application"; ENERGIES, vol. 12, No. 9, 1731, May 8, 2019 (16 pages).

Kamal, M.S., et al.; "A Zwitterionic Surfactant Bearing Unsaturated Tail for Enhanced Oil Recovery in High-Temperature High-Salinity Reservoirs"; Journal of Surfactants and Detergents, vol. 21, No. 1, Jan. 2018, pp. 165-174 (10 pages).

Kamal Muhammad Shahzad: "A Review of Gemini Surfactants: Potential Application in Enhanced Oil Recovery", Journal of Surfactants and Detergents, Springer, Berlin, DE, vol. 19, No. 2, Dec. 26, 2015, pp. 223-236 (14 pages).

International Search Report and Written Opinion issued in Application No. PCT/US2020/040635, dated Mar. 5, 2021 (13 pages).

\* cited by examiner

METHODS AND COMPOSITIONS OF USING VISCOELASTIC SURFACTANTS AS DIVERSION AGENTS

Well stimulation enables the improved extraction of hydrocarbon reserves that conventional recovery processes, such as gas or water displacement, cannot access. One well stimulation technique is matrix stimulation, which may also be referred to as matrix acidizing treatment. In matrix stimulation, an acidic fluid is injected into a formation at a pressure below the fracture pressure and is used to stimulate a reservoir by reacting with the reservoir rock, thereby dissolving the rock to create a pathway for hydrocarbon production.

However, when the acidic fluid has a low viscosity, the acid may have limited penetration into the formation and only react at the face of the rock. This is not an effective method for stimulating the reservoir as a conductive pathway for hydrocarbon production is not created. Further, most of the reservoirs have heterogeneous permeabilities which result in the low viscosity acid primarily penetrating the high permeable zones in the reservoir and leaving most of the low permeability zones untreated.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to wellbore fluids that include a gemini surfactant, a zwitterionic surfactant, an activator, and an aqueous base fluid. The gemini surfactant may have a structure represented by formula (I):

In another aspect, embodiments disclosed herein relate to methods for treating a hydrocarbon-containing formation, the methods including injecting a wellbore fluid into a high permeability zone of a hydrocarbon-containing formation. The high permeability zone may increase the temperature of the wellbore fluid, resulting in the wellbore fluid having an increased viscosity. The wellbore fluids may include a gemini surfactant, a zwitterionic surfactant, an activator, and an aqueous base fluid. The gemini surfactant may have a structure represented by the above formula (I).

In another aspect, embodiments disclosed herein relate to methods for stimulating the recovery of hydrocarbons from a hydrocarbon-containing formation, the methods including injecting a wellbore fluid into a high permeability zone of a hydrocarbon-containing formation, stimulating the hydrocarbon-containing formation using the wellbore fluid thereby creating pathways for hydrocarbon production, and recovering the hydrocarbons. The high permeability zone may increase the temperature of the wellbore fluid, resulting in the wellbore fluid having an increased viscosity. The wellbore fluids may include a gemini surfactant, a zwitterionic surfactant, an activator, and an aqueous base fluid. The gemini surfactant may have a structure represented by the above formula (I).

In another aspect, embodiments disclosed herein relate to methods of preparing a wellbore fluid, the methods including mixing a gemini surfactant, a zwitterionic surfactant, an activator, and an aqueous base fluid. The gemini surfactant may have a structure represented by the above formula (I).

In a further aspect, embodiments disclosed herein relate to a gemini surfactant having a structure represented by the above formula (I).

Other aspects and advantages of the claimed subject matter will be apparent from the following description and the appended claims.

DETAILED DESCRIPTION

Figure 1:
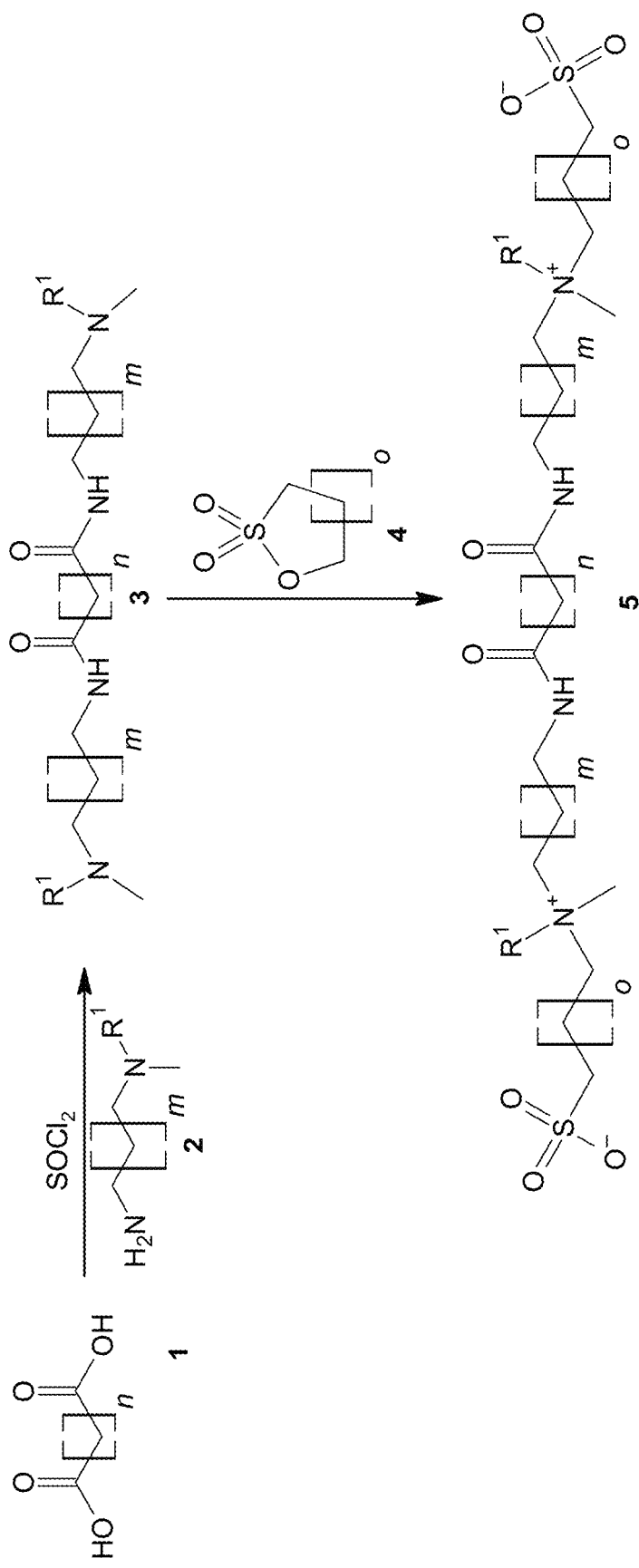
FIG. 1 is schematic representation of the synthesis of a surfactant of one or more embodiments.

Embodiments in accordance with the present disclosure generally relate to a gemini surfactant, wellbore fluids that contain one or more surfactants and an activator, and methods of using the fluids in processes such as acid stimulation,

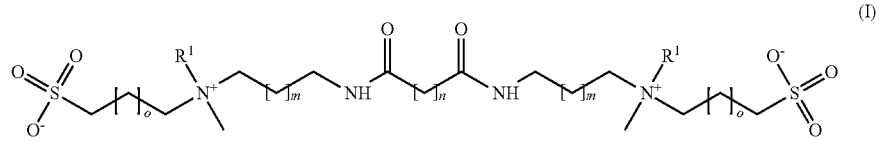

(I)

where $R^1$ is a $C_1$-$C_{10}$ hydrocarbon group, m and o are each, independently, an integer ranging from 1 to 4, and n is an integer ranging from 8 to 12.

enhanced oil recovery (EOR) and fracturing. The surfactants may be viscoelastic. Methods of one or more embodiments may involve injecting the wellbore fluids into a formation, exposing the fluid to an increased temperature and resulting in the wellbore fluid having an increased viscosity. Such methods may modify the injection profile of the formation a well stimulation treatment by diverting stimulation fluid to lower permeability zones of the reservoir.

The wellbore fluids may be low-viscosity aqueous solutions that increase in viscosity under downhole conditions. The wellbore fluids may demonstrate increased stability under high temperature and pressure conditions, making them highly suitable for use in downhole environments. When the wellbore fluid contacts a produced hydrocarbon its viscosity may drastically reduce, enabling easy flowback of the fluid post treatment. As the viscosifying material used in the present disclosure does not contain any solid particulates, it will be potentially non-damaging to the formation due to effective flowback and no residual deposition inside the formation.

One or more embodiments of the present disclosure are directed to a gemini surfactant. As used herein, the term "gemini surfactant" generally refers to surfactant that comprises two surfactant moieties that are chemically bonded via a spacer group. The surfactant moieties may contain a hydrophilic head group and a hydrophobic tail. The two surfactant moieties may be the same as, or different from, one another. In one or more embodiments, the gemini surfactant may include surfactant moieties having a cationic head group. In particular embodiments, the surfactant moieties may include a quaternary ammonium group. The gemini surfactant of one or more embodiments may further comprise one or more amide groups and one or more sulfonate groups.

In one or more embodiments, the gemini surfactant may have a structure represented by formula (I):

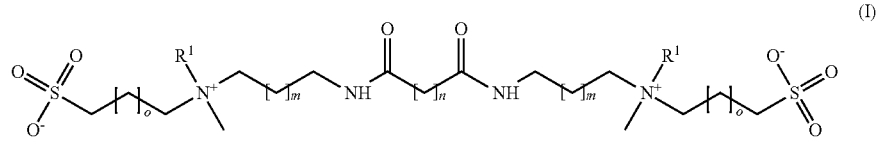

(I)

where $R^1$ is a $C_1$-$C_{10}$ hydrocarbon group, m and o are each, independently, an integer ranging from 1 to 4, and n is an integer ranging from 8 to 12.

As used herein with regard to group $R^1$, the term "hydrocarbon group" refers to branched, straight chain, and ring-containing hydrocarbon groups, any of which may be saturated or unsaturated. The hydrocarbon groups may be primary, secondary, and/or tertiary hydrocarbons.

In one or more embodiments, the gemini surfactant may be highly soluble in aqueous solutions, such as in deionized water, seawater, brines, calcium chloride solutions, and the like. In some embodiments, the gemini surfactant may be soluble in aqueous solutions in an amount of 10% by weight (wt. %) or more, 20 wt. % or more, 30 wt. % or more, or 40 wt. % or more at ambient temperature. In some embodiments, the solubility of the gemini surfactant may increase with increasing temperature, until gelation occurs.

In one or more embodiments, the gemini surfactant may be thermally stable at a temperature of 200° C. or more, 250° C. or more, 300° C. or more, or 350° C. or more, as measured by thermogravimetric analysis (TGA).

One or more embodiments of the present disclosure are directed to wellbore fluids. The wellbore fluids of one or more embodiments may include, for example, water-based wellbore fluids. The wellbore fluids may be acid stimulation fluids, EOR fluids or fracturing fluids, among others.

In one or more embodiments, the water-based wellbore fluids may comprise an aqueous fluid. The aqueous fluid may include at least one of fresh water, seawater, brine, water-soluble organic compounds, and mixtures thereof. The aqueous fluid may contain fresh water formulated to contain various salts in addition to the first or second salt, to the extent that such salts do not impede the desired nitrogen-generating reaction. The salts may include, but are not limited to, alkali metal halides and hydroxides. In one or more embodiments, brine may be any of seawater, aqueous solutions wherein the salt concentration is less than that of seawater, or aqueous solutions wherein the salt concentration is greater than that of seawater. Salts that are found in seawater may include sodium, calcium, aluminum, magnesium, potassium, strontium, and lithium salts of halides, carbonates, chlorates, bromates, nitrates, oxides, phosphates, among others. Any of the aforementioned salts may be included in brine. In one or more embodiments, the density of the aqueous fluid may be controlled by increasing the salt concentration in the brine, though the maximum concentration is determined by the solubility of the salt. In particular embodiments, brine may include an alkali metal halide or carboxylate salt and/or alkaline earth metal carboxylate salts.

The wellbore fluids include one or more surfactants. In one or more embodiments, the surfactants may include a gemini surfactant as discussed above. In particular embodiments, the gemini surfactant may have a structure represented by formula (I) above.

The wellbore fluids of one or more embodiments may comprise the gemini surfactant in an amount of the range of about 1 to 15% by weight (wt. %). For example, the wellbore fluid may contain the gemini surfactant in an amount ranging from a lower limit of any of 1, 1.5, 2, 2.5, 3, 4, 5, 7, 10, and 12 wt. % to an upper limit of any of 1.5, 2, 3, 4, 5, 6, 8, 10, 12, 14, and 15 wt. %, where any lower limit can be used in combination with any mathematically-compatible upper limit.

In one or more embodiments, the wellbore fluids may contain a gemini surfactant in combination with one or more additional surfactants. In particular embodiments, the wellbore fluids may contain a gemini surfactant and a zwitterionic surfactant. The zwitterionic surfactant may be any of those known to one of ordinary skill in the art and may be, for instance, derived from a betaine in particular embodiments. In some embodiments, the zwitterionic surfactant may include a quaternary ammonium group and a sulfonate group. The zwitterionic surfactant of one or more embodiments may further comprise an amide group.

In one or more embodiments, a zwitterionic surfactant may have a structure represented by formula (II):

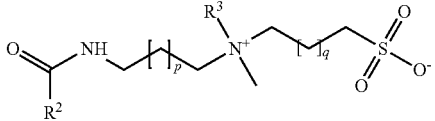

(II)

where $R^2$ is a $C_{15}$-$C_{27}$ hydrocarbon group or a $C_{15}$-$C_{29}$ substituted hydrocarbon group, $R^3$ is a $C_1$-$C_{10}$ hydrocarbon group, and p and q are each, independently, an integer ranging from 1 to 4.

In reference to $R^2$ and $R^3$, the term "hydrocarbon group" has the same meaning as discussed above with regard to $R^1$. As used with regard to $R^2$, the term "substituted hydrocarbon group" refers to a hydrocarbon group (as defined above) where at least one hydrogen atom is substituted with a non-hydrogen group that results in a stable compound. Such substituents may be groups selected from, but not limited to, halo, hydroxyl, alkoxy, oxo, alkanoyl, aryloxy, alkanoyloxy, amino, alkylamino, arylamino, arylalkylamino, disubstituted amines, alkanylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide, substituted sulfonamide, nitro, cyano, carboxy, carbamyl, alkoxycarbonyl, aryl, substituted aryl, guanidine, and heterocyclyl, and mixtures thereof. In some embodiments, the substituted hydrocarbon group may comprise one or more alkylene oxide units. The alkylene oxide may be ethylene oxide.

In one or more embodiments, the zwitterionic surfactant may be soluble in aqueous solutions, such as in deionized water, seawater, brines, calcium chloride solutions, and the like. In some embodiments, the zwitterionic surfactant may be soluble in aqueous solutions in an amount of 10% by weight (wt. %) or more, 20 wt. % or more, or 30 wt. % or more at ambient temperature. In some embodiments, the zwitterionic surfactant may have a lower aqueous solubility than the gemini surfactant. In some embodiments, the solubility of the zwitterionic surfactant may increase with increasing temperature, until gelation occurs.

The wellbore fluids of one or more embodiments may comprise the zwitterionic surfactant in an amount of the range of about 1 to 15% by weight (wt. %). For example, the wellbore fluid may contain the zwitterionic surfactant in an amount ranging from a lower limit of any of 1, 1.5, 2, 2.5, 3, 4, 5, 7, 10, and 12 wt. % to an upper limit of any of 1.5, 2, 3, 4, 5, 6, 8, 10, 12, 14, and 15 wt. %, where any lower limit can be used in combination with any mathematically-compatible upper limit.

In one or more embodiments, the wellbore fluid may comprise the gemini surfactant and the zwitterionic surfactant in a weight ratio of 1:5 to 5:1 by weight, where the weight ratio is given as the weight of the gemini surfactant to the weight of the zwitterionic surfactant. For example, the wellbore fluid may contain the gemini surfactant and the zwitterionic surfactant in a weight ratio ranging from a lower limit of any of 1:5, 1:4, 1:3, 1:2, 1:1, and 2:1, to an upper limit of any of 1:2, 1:1, 2:1, 3:1, 4:1, and 5:1, where any lower limit can be used in combination with any mathematically-compatible upper limit.

The wellbore fluids of one or more embodiments may have a total surfactant content, including both a gemini and zwitterionic surfactant, in an amount of the range of about 1 to 30% by weight (wt. %). For example, the wellbore fluid may have a total surfactant content in an amount ranging from a lower limit of any of 1, 2, 2.5, 3, 4, 5, 7, 10, 12, 15, 20, and 25 wt. % to an upper limit of any of 1.5, 2, 3, 4, 5, 6, 8, 10, 12, 15, 20, 25, and 30 wt. %, where any lower limit can be used in combination with any mathematically-compatible upper limit.

The wellbore fluids may include an activator. The activator is an additive that, upon an increase in temperature, enables the surfactant to exhibit viscoelastic behavior and cause the wellbore fluid to increase in viscosity. Without being bound by any theory, the activators disclosed herein may enable the surfactant micelles to form a rod-shaped structure that entangle as the temperature of the fluid increases. This entanglement is the cause of the viscoelastic behavior and the increase in viscosity.

In one or more embodiments, the activator may be a salt. The salt may, for instance comprise a monovalent cation, such as an alkali metal or a Group 11 transition metal, or a divalent cation, such as an alkaline earth metal or a transition metal. In some embodiments, the salt may comprise a cation selected from the group consisting of lithium, sodium, potassium, magnesium, calcium, nickel, iron, tin, aluminum, and zinc. In some embodiments, the salt may comprise an anion selected from the group consisting of fluoride, chloride, bromide, carbonate, bicarbonate, sulfate, nitrate, nitrite, chromate, sulfite, oxalate, phosphate, and phosphite. In particular embodiments, the activator may be an alkaline earth metal halide, such as calcium chloride.

The wellbore fluids of one or more embodiments may comprise the activator in an amount of the range of about 5 to 30% by weight (wt. %). For example, the wellbore fluid may contain the activator in an amount ranging from a lower limit of any of 5, 6, 7, 8, 10, 12, 15, 17, 20, and 22 wt. % to an upper limit of any of 10, 12, 15, 17, 20, 22, 25, 27, and 30 wt. %, where any lower limit can be used in combination with any mathematically-compatible upper limit.

In one or more embodiments, the wellbore fluid may comprise the activator and the surfactants in a weight ratio of 30:1 to 1:3, by weight, where the weight ratio is given as the weight of the activator to the total weight of the surfactants. For example, the wellbore fluid may contain the activator and the surfactants in a weight ratio ranging from a lower limit of any of 1:3, 1:2, 1:1, 2:1, 4:1, 6:1, 8:1, 10:1 and 12:1 to an upper limit of any of 1:1, 2:1, 4:1, 6:1, 8:1, 10:1, 12:1, 15:1, 20:1, 25:1, and 30:1, where any lower limit can be used in combination with any mathematically-compatible upper limit.

The wellbore fluids of one or more embodiments may include one or more acids. Acids may be particularly included when the wellbore fluid is to be used in a matrix stimulation process, as described below. The acid may be any suitable acid known to a person of ordinary skill in the art, and its selection may be determined by the intended application of the fluid. In some embodiments, the acid may be one or more selected from the group consisting of hydrochloric acid, sulfuric acid, carboxylic acids such as acetic acid, and hydrofluoric acid. In some embodiments, the hydrofluoric acid may be included as a hydrogen fluoride source, such as ammonium fluoride, ammonium bifluoride, fluoroboric acid, hexafluorophosphoric acid, and the like.

The wellbore fluid of one or more embodiments may comprise the one or more acids in a total amount of the range of about 0.01 to 30.0 wt. %. For example, the wellbore fluid may contain the acids in an amount ranging from a lower limit of any of 0.01, 0.05, 0.1, 0.5, 1.0, 5.0, 10, 15, 20, and 25 wt. % to an upper limit of any of 0.5, 1.0, 5.0, 10, 15, 20, 25, and 30 wt. %, where any lower limit can be used in combination with any mathematically-compatible upper limit.

The wellbore fluids of one or more embodiments may include one or more additives. The additives may be any conventionally known and one of ordinary skill in the art will, with the benefit of this disclosure, appreciate that the selection of said additives will be dependent upon the intended application of the wellbore fluid. For instance, if the wellbore fluid is to be used as a fracturing fluid, it may comprise a proppant such as sand. In some embodiments, the additives may be one or more selected from clay stabilizers, scale inhibitors, corrosion inhibitors, biocides, friction reducers, thickeners, and the like.

The wellbore fluid of one or more embodiments may comprise the one or more additives in a total amount of the range of about 0.01 to 15.0 wt. %. For example, the wellbore fluid may contain the additives in an amount ranging from a lower limit of any of 0.01, 0.05, 0.1, 0.5, 1.0, 2.5, 5.0, 1.5, 10.0 and 12.5 wt. % to an upper limit of any of 0.1, 0.5, 1.0, 2.5, 5.0, 7.5, 10.0, 12.5, and 15.0 wt. %, where any lower limit can be used in combination with any mathematically-compatible upper limit.

In one or more embodiments, the wellbore fluid may contain little to no solid material. For example, the wellbore fluids of some embodiments may contain solid material in an amount of 2 wt. % or less, 1 wt. % or less, 0.5 wt. % or less, 0.1 wt. % or less, 0.05 wt. % or less, 0.01 wt. % or less, or 0.001 wt. % or less.

In one or more embodiments, the wellbore fluid may have a density that is greater than 0.90 g/cm$^3$. For example, the wellbore fluid may have a density that is of an amount ranging from a lower limit of any of 0.90, 0.95, 1.00, 1.05, 1.10, 1.15, and 1.20 g/cm$^3$ to an upper limit of any of 1.00, 1.05, 1.10, 1.15, 1.20, and 1.25 g/cm$^3$, where any lower limit can be used in combination with any mathematically-compatible upper limit.

In one or more embodiments, the wellbore fluid may have a viscosity at 40° C. that is of the range of about 1 to 20 cP. For example, the wellbore fluid may have a viscosity at 40° C. that is of an amount ranging from a lower limit of any of 1, 2, 3, 4, 5, 6, 7, 8, 10, and 12 cP to an upper limit of any of 4, 5, 6, 8, 10, 12, 14, 16, 18, and 20 cP, where any lower limit can be used in combination with any mathematically-compatible upper limit. In some embodiments, the wellbore fluids may have a viscosity at 40° C. of 20 cP or less, 15 cP or less, or 10 cP or less.

In one or more embodiments, the wellbore fluid may have a viscosity at 90° C. that is of the range of about 8 to 100 cP. For example, the wellbore fluid may have a viscosity at 90° C. that is of an amount ranging from a lower limit of any of 8, 9, 10, 12, 15, 20, 30, 40, 50, 60, and 80 cP to an upper limit of any of 10, 12, 15, 20, 30, 40, 50, 60, 70, 90, and 100 cP, where any lower limit can be used in combination with any mathematically-compatible upper limit. In some embodiments, the wellbore fluids may have a viscosity at 90° C. of 10 cP or more, 20 cP or more, 30 cP or more, or 40 cP or more.

The wellbore fluid of one or more embodiments may have a viscosity that is higher at 90° C. than at 40° C. In one or more embodiments, the wellbore fluid may have a ratio of a viscosity at 90° C. to a viscosity at 40° C. that is of the range of about 3:1 to 25:1. For example, the wellbore fluids may have a ratio of a viscosity at 90° C. to a viscosity at 40° C. that is of the range having a lower limit of any of 3:1, 4:1, 5:1, 6:1, 8:1, 10:1, and 12:1 to an upper limit of any of 10:1, 12:1, 15:1, 20:1, and 25:1, where any lower limit can be used in combination with any mathematically-compatible upper limit.

In one or more embodiments, the viscosity of the wellbore fluid may decrease after contacting with a hydrocarbon. For example, after contacting with a hydrocarbon such as diesel, the wellbore fluid may have a viscosity at 90° C. that is of an amount ranging from a lower limit of any of 1, 2, 3, 4, 5, 6, 7, 8, and 10, cP to an upper limit of any of 2, 4, 6, 8, 10, 12, and 15 cP, where any lower limit can be used in combination with any mathematically-compatible upper limit. In some embodiments, after contacting with a hydrocarbon such as diesel, the wellbore fluid may have a viscosity at 90° C. of 15 cP or less, 12 cP or less, 10 cP or less, 8 cP or less, or 5 cP or less.

In one or more embodiments, the wellbore fluid may have a pH that is neutral or acidic. For example, the wellbore fluid may have a pH ranging from a lower limit of any of 2, 3, 4, 4.5, 5, 5.5, and 6, to an upper limit of any of 3, 4, 4.5, 5, 5.5, 6, 6.5, and 7, where any lower limit can be used in combination with any mathematically-compatible upper limit. In some embodiments, the wellbore fluid may have a pH of 7 or less, of 6 or less, of 5 or less, of 4 or less, or of 3 or less.

One or more embodiments of the present disclosure are directed to a synthesis of the surfactants represented by the aforementioned formula (I). A synthesis of one or more embodiments is depicted in FIG. 1, wherein $R^1$, m, n, and o represent the same groups as discussed above with regard to formula (I).

As shown by FIG. 1, a dicarboxylic acid 1 and an amine 2 may undergo an amidation reaction to yield intermediate amide 3. In one or more embodiments, an excess amount of amine 2 is used. In some embodiments, a molar ratio of amine 2 to dicarboxylic acid 1 is in a range of 2:1 to 5:1, or 5:2 to 4:1.

In one or more embodiments, the dicarboxylic acid 1 is converted in situ to an acyl chloride before reaction with the amide 2. In such embodiments, a conventional chlorinating reagent, such as thionyl chloride, may be used. The dicarboxylic acid 1 may be added to the chlorinating reagent at a temperature below room temperature, such as at a temperature in the range of about −10 to 10° C., or about 0° C. The temperature may then be increased to room temperature while the reaction occurs. The chlorinating reagent and the dicarboxylic acid 1 may be allowed to react for 6-20 hours, 8-16 hours, or about 12 hours. The mixture may be agitated throughout the duration of the reaction by any method known to a person of ordinary skill in the art, such as by employing a rotary shaker, a magnetic stirrer, or an overhead stirrer. Excess chlorinating reagent may be removed by bubbling of inert gas, such as $N_2$. The acyl chloride of acid 1 may be generated in an approximately quantitative yield. The amine 2 may be dissolved in a solvent, such as dichloromethane, chloroform, or dichloroethane, and added slowly to the acyl chloride of acid 1. In some embodiments, the amine solution may be added dropwise. In some embodiments, the acyl chloride of acid 1 may be at a temperature below room temperature, such as at a temperature in the range of about −10 to 10° C., or about 0° C., when the amine 2 solution is added. The temperature may then be increased to room temperature while the reaction occurs. The acid chloride of acid 1 and the amine 2 may be allowed to react for 6-20 hours, 8-16 hours, or about 12 hours. The mixture may be agitated throughout the duration of the reaction by any method discussed above. The amidation reaction may be conducted under an inert atmosphere, such as under one or more of nitrogen, argon, and helium gas. After the reaction, the residue may be extracted from one or more of the group consisting of chloroform, dichloromethane, ethyl acetate, and iso-propanol and subsequently dried under vacuum to yield intermediate amide 3. The intermediate amide 3 may be produced in a yield of 75% or more, 80% or more, 85% or more, 90% or more, 95% or more, or 97% or more.

In one or more embodiments, the reaction between the acyl chloride of acid 1 and amine 2 may further include the use of an amine to facilitate the amidation. The amine catalyst may be triethylamine. A molar ratio of the amine to the acyl chloride of acid 1 may be in a range of 1:1 to 10:1, or about 4:1 to 8:1.

In alternative embodiments, the fatty acid 1 may not be converted to the acid chloride first, but instead directly reacted with the amine 2. In such instances, the amidation reaction may be performed at reflux. In some embodiments, the reaction is performed at a temperature that is of the range of 100 to 200° C., 140 to 180° C., or about 160° C. An external heat source, such as an oil bath, an oven, microwave, or a heating mantle, may be employed to heat the mixture to the aforementioned temperature. The mixture may be agitated throughout the duration of the reaction by any method known to a person of ordinary skill in the art, such as by employing a rotary shaker, a magnetic stirrer, or an overhead stirrer. In one or more embodiments, the amine 2 may be added in a two-stage or multi-stage fashion. For example, a first portion of the amine 2 of 50-70%, 55-65%, or about 57% of the total moles of the amine 2 used herein, may be added to the mixture and allowed to react with the dicarboxylic acid 1 for 4-12 hours, 6-10 hours, or about 8 hours, and subsequently a second portion of the amine which is 30-50%, 35-45%, or about 43% of the total moles of the amine used herein may be added to the same mixture and allowed to react with the dicarboxylic acid for a duration of 3-9 hours, 5-7 hours, or about 6 hours. Alternatively, the amine may be introduced to the mixture in one batch and allowed to react with the carboxylic acid for 6-20 hours, 8-16 hours, or about 12 hours. In one or more embodiments, the reaction between dicarboxylic acid 1 and amine 2 may further include the use of a fluoride catalyst to facilitate the amidation. The fluoride catalyst may be one or more selected from the group consisting of sodium fluoride, potassium fluoride, silver fluoride, cesium fluoride, and tetrabutylammonium fluoride. A molar ratio of the fluoride catalyst to dicarboxylic acid 1 may be in a range of 1:5 to 1:20, 1:8 to 1:12, or about 1:10.

Subsequently, as shown in FIG. 1, amide 3 may be reacted with a sultone 4 to yield a surfactant 5 having a structure consistent with formula (I). In one or more embodiments, a molar ratio of the sultone 4 to the amide 3 is in a range of 4:1 to 1:2, 3:1 to 1:1, or about 3:2. In some embodiments, the reaction may be performed with a molar excess of sultone 4. In one or more embodiments, this reaction is conducted in a polar aprotic solvent, such as one or more selected from the group consisting of ethyl acetate, dimethylformamide, tetrahydrofuran, acetone, acetonitrile, and dimethyl sulfoxide. In some embodiments, the reaction may be adapted to be performed in polar protic solvents such as one or more selected from the group consisting of methanol, ethanol, propanol, isopropyl alcohol, and butanol. In one or more embodiments, reacting the intermediate amide 3 with the sultone 4 is conducted without a solvent. In one or more embodiments, the reaction may be performed at reflux. In some embodiments, the reaction is performed at a temperature that is of the range of 50 to 100° C., 60 to 90° C., or about 80° C. In one or more embodiments, the reaction may have a duration of and has a reaction time of 2 to 36 hours, 2 to 24 hours, 4 to 16 hours, 10 to 14 hours, or about 12 hours. After the reaction, the solid residue may be collected and washed with a solvent selected from one or more of the group consisting of ethyl acetate and diethyl ether and subsequently dried under vacuum to yield surfactant 5 as a white solid. The surfactant 5 may be produced in a yield of 75% or more, 80% or more, 85% or more, 90% or more, 95% or more, or 97% or more.

Methods in accordance with the present disclosure may comprise the injection of a wellbore fluid into a formation. In one or more embodiments, the wellbore fluid may be a single treatment fluid that is injected into the wellbore in one pumping stage. In other embodiments, methods in accordance with one or more embodiments may involve the injection of the wellbore fluid and one or more additional stimulation fluids. The additional stimulation fluids may, in some embodiments, be co-injected with the wellbore fluid. In some embodiments, the stimulation fluids may be injected after the wellbore fluid.

The wellbore fluid of one or more embodiments has a low viscosity at low temperatures and, therefore, good injectivity, while being thermally stable enough for use downhole. Upon exposure to increased temperatures in the wellbore, the wellbore fluid may increase in viscosity. This phenomenon has the effect of reducing fluid mobility, resulting in diverting the flow from high permeability zones to lower ones and, ultimately, providing improved oil recovery.

The methods of one or more embodiments of the present disclosure may further comprise a pre-flushing step before the injection of the wellbore fluid. The pre-flushing step may comprise flushing the formation with a flushing solution that comprises one or more surfactants. The flushing solution may be an aqueous solution, and the surfactant may be the same surfactants as included in the wellbore fluid. The pre-flushing may limit the adsorption of the surfactants on the rock surface of the formation during the injection process. The suitability of the use of a pre-flushing step may depend on the type of surfactant and rock.

The hydrocarbon-containing formation of one or more embodiments may be a formation containing multiple zones of varying permeability. For instance, the formation may contain at least a zone having a relatively higher permeability and a zone having a relatively lower permeability. During conventional injection, fluids preferentially sweep the higher permeability zone, leaving the lower permeability zone incompletely swept. In one or more embodiments, the increased viscosity of the wellbore fluid may "plug" the higher permeability zone, allowing subsequent fluid to sweep the low permeability zone and improving sweep efficiency.

In one or more embodiments, the formation may have a temperature ranging from about 60 to 250° C. For example, the formation may have a temperature that is of an amount ranging from a lower limit of any of 60, 70, 80, 90, 100, 120, 140, 160, 180, and 200° C. to an upper limit of any of 100, 120, 140, 160, 180, 200, 225, and 250° C., where any lower limit can be used in combination with any mathematically-compatible upper limit.

Figure 2:
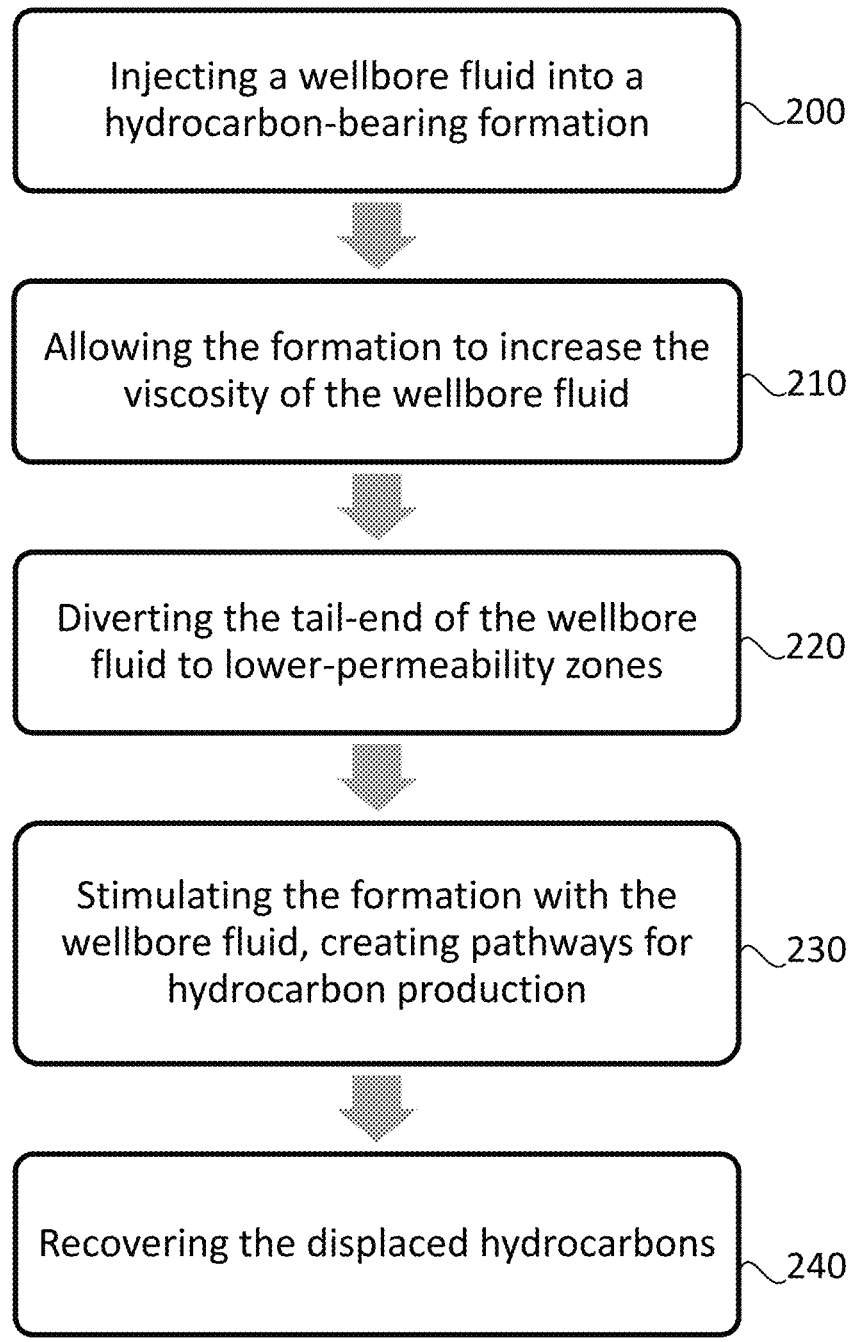
FIG. 2 is a flowchart depicting a well stimulation process in accordance with one or more embodiments of the present disclosure.

The methods of one or more embodiments may be used for well stimulation. A well stimulation process in accordance with one or more embodiments of the present disclosure is depicted by, and discussed with reference to, FIG. 2. Specifically, in step 200, the wellbore fluid may be injected into a hydrocarbon-bearing formation at an injection well. In some embodiments, the injection of the wellbore fluid may be performed at a pressure that is below the fracturing pressure of the formation. In step 210, a zone within the formation may be at a high temperature and increase the viscosity of the wellbore fluid. In step 220, after the increase in viscosity, the tail-end of the fluid is diverted to lower-permeability zones of the formation, displacing hydrocarbons. This results from the increase in viscosity that may "plug" the more permeable zones of the formation. In step 230, the formation is stimulated by the wellbore fluid, creating pathways for hydrocarbon production. In step 240, the displaced hydrocarbons may be recovered through the stimulated reservoir. In one or more embodiments, the hydrocarbons may be recovered at a production well.

The well stimulation process of one or more embodiments may be a matrix stimulation process. In the matrix stimulation process of one or more embodiments, the wellbore fluid, or one of the stimulation fluids, contains an acid. The acid fluid may react with the formation, dissolving rock, and creating wormholes that create a pathway for hydrocarbons to be displaced from deeper within the rock. In one or more embodiments, the wellbore fluid may increase in viscosity in the formation, enabling the fluid to better penetrate lower-permeability zones of the formation and allowing the acid to more uniformly react with the entire formation. This may provide for the formation of deeper wormholes and enhancing the overall permeability of the near-wellbore region. In the absence of this viscosity increase, the fluid will primarily penetrate the high permeability zones.

In one or more embodiments, the well stimulation process may be repeated one or more times to increase the amount of hydrocarbons recovered. In some embodiments, subsequent well stimulation processes may involve the use of different amounts of the surfactant and/or different surfactants than the first. The methods of one or more embodiments may advantageously provide improved sweep efficiency.

The methods of one or more embodiments may be used for fracturing a formation. In these embodiments, the wellbore fluid may be injected into a hydrocarbon-bearing formation at an injection well. The fluid may be driven through the formation at a pressure higher than the formation, opening pores and cracks present in the formation. The wellbore fluid of one or more embodiments may contain a proppant, such as sand, that can keep the pores and cracks of the formation open. These processes may, therefore, increase the permeability and hydrocarbon flow of the formation.

Examples

The following examples are merely illustrative and should not be interpreted as limiting the scope of the present disclosure.

Figure 3:
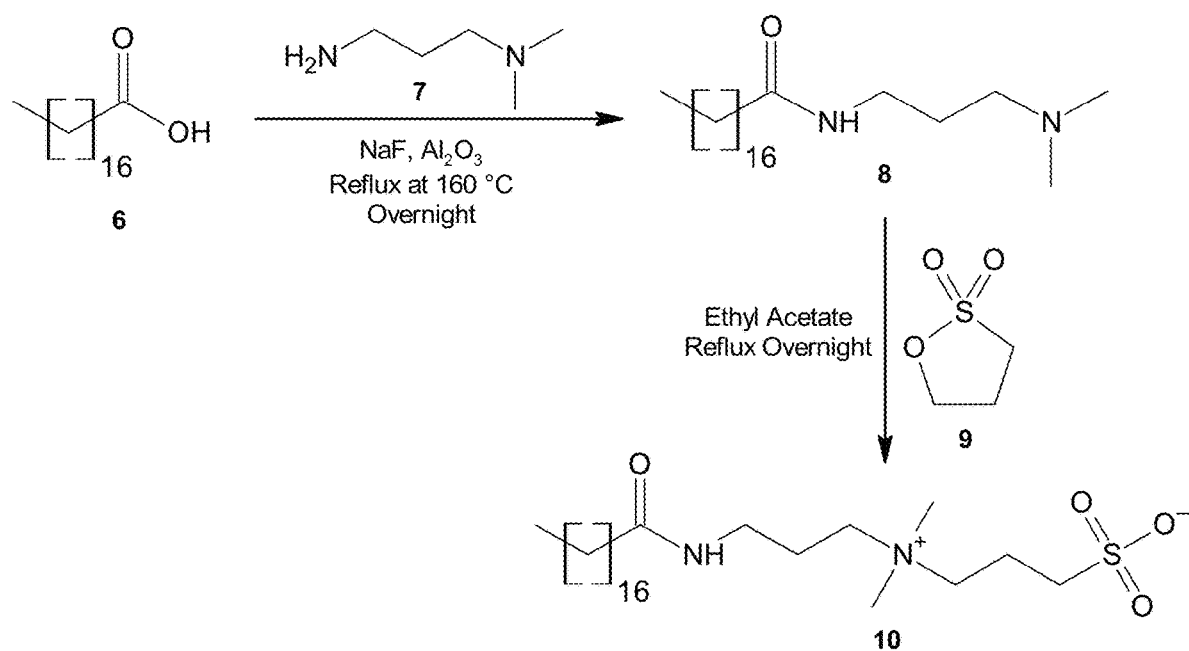
FIG. 3 is a schematic representation of the synthesis of an exemplary zwitterionic surfactant.

A zwitterionic surfactant 10 was prepared by the synthetic route illustrated in FIG. 3. Specifically, the zwitterionic surfactant 10 was synthesized by initially preparing the intermediate 8, and then then reacting 8 with 1,3-propanesultone 9.

Synthesis of N-(3-(dimethylamino)propyl)nonadecanamide (8):

A two-necked round bottom flask, fixed with a reflux condenser and a bent tube, was charged with stearic acid 6 (5.00 g, 20.63 mmol), 3-(dimethylamino)-1-propylamine 7 (4.22 g, 41.25 mmol), and NaF (0.09 g, 2.06 mmol). The bent tube was filled with well dried alumina, which absorbs any water generated by the reaction. The flask was heated at a temperature of 160° C. for eight hours under a $N_2$ atmosphere. A second aliquot of 3-(dimethylamino)-1-propylamine 7 (30.94 mmol) was added and the conditions were maintained for a further six hours. After cooling to room temperature, the solid residue was collected, washed with cold acetone: water (93:7 mL), and dried under vacuum to yield a white solid 8. $^1$H-NMR [$CD_3OD$]=0.869 (t, 3H), 1.451-1.521 (m, 27H), 1.240-1.657 (m, 4H), 2.133 (t, 2H), 2.224 (s, 6H), 2.334 (t, 2H), 3.332 (t, 2H); $^{13}$C-NMR [$CD_3OD$]=18.95, 22.14, 25.22, 28.11, 33.32, 35.68, 35.88, 44.02, 50.66, 61.57, 63.46, 177.53, 180.53.

Synthesis of 3-(metheyliumyl(methyl)(3-stearamidopropyl)-14-azaneyl)propane-1-sulfonate (SDAS, 10):

A 250-mL two-necked flask fixed with a reflux condenser was charged with 8 (5.00 g, 15.31 mmol), 1,3-propanesultone 9 (2.81 g, 22.97 mmol), and ethyl acetate (100 mL). The flask was heated at 80° C. for 12 h. After cooling to room temperature, the solid was collected, washed successively using ethyl acetate (100 mL) and diethyl ether (50 mL), and dried under vacuum to yield SDAS 10 as a white solid (6.14 g, 89% yield). $^1$H-NMR [$CDCl_3$]$_{=1.101}$ (t, 3H), 1.451-1.521 (m, 27H), 1.805 (m, 2H), 2.185 (t, 2H), 2.324-2.425 (m, 4H), 3.075 (t, 2H), 3.473 (t, 2H), 3.54 (s, 6H), 3.726 (t, 2H); $^{13}$C-NMR [$CD_3OD$]=14.0, 19.3, 22.6, 23.0, 25.9, 29.3, 29.6, 29.7, 31.9, 36.3, 36.4, 48.1, 50.9, 62.6, 63.2, 174.6; FTIR ($cm^{-1}$)=3265.42, 2915.00, 2884.61, 1666.49, 1552.64, 1467.54, 1174.26,1035.13, 723.06.

Figure 4:
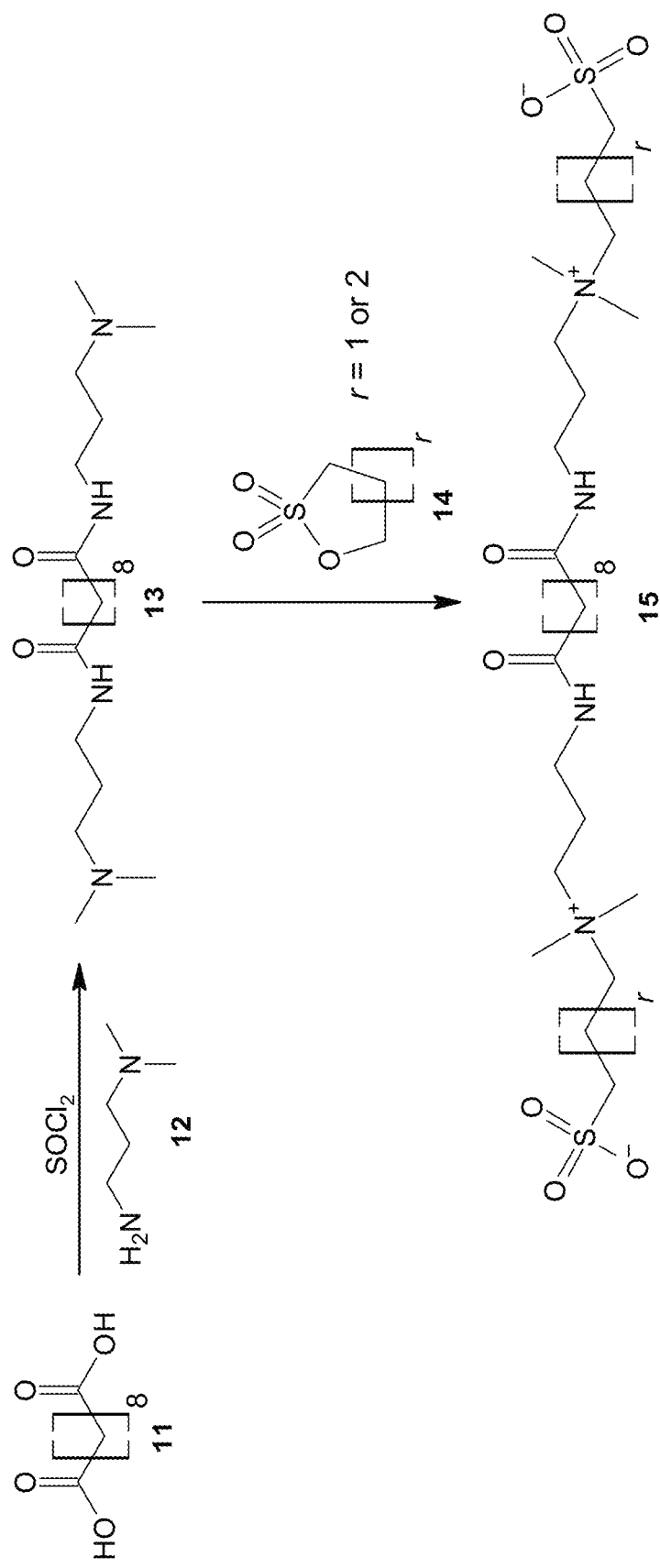
FIG. 4 is a schematic representation of the synthesis of an exemplary gemini surfactant.

Two gemini surfactants 15.1 (r=1) and 15.2 (r=2) were prepared by the synthetic route illustrated in FIG. 4. Specifically, the surfactants 15 whereas synthesized by initially preparing the intermediate 13, and reacting 13 with either 1,3-propane sultone or 1,4-propane sultone 13.

Synthesis of $N^1$, $N^{10}$-bis(3-(dimethylamino)propyl)decanediamide (13)

Thionyl chloride (10 mL) was taken in the round bottom flask and cold to 0° C. in an ice bath. Then, sebacic acid 11 (24.72 mmol) was added slowly with continuous stirring in the reaction flask. The temperature was slowly raised to room temperature and the stirring was continued overnight. Upon completion of the reaction, $N_2$ was bubbled through the reaction mixture to eliminate the excessive thionyl chloride keeping the reaction flask in fume hood followed by vacuum drying on rotavapor. The acid chloride product was received in a quantitative yield. $N^1$, $N^1$-dimethylpropane-1, 3-diamine 12 (2.5 eq) was taken in another round bottom flask and cold to 0° C. in an ice bath. Dichloromethane was added to the flask followed by addition of triethylamine (6.0 eq). The acid chloride was dissolved in dichloromethane and the resulting solution was added dropwise to the reaction flask at 0° C. and the reaction allowed to reach room temperature where it was stirred overnight. $N^1$, $N^{10}$-bis(3-(dimethylamino)propyl)decanediamide 13 was isolated from the mixture. $^1$H-NMR [CDCl$_3$] =1.255-1.302 (m, 8H), 1.577 (m, 4H), 1.637 (t, 4H), 2.121 (t, 4H), 2.280 (s, 12H), 2.367 (t, 4H), 3.319 (t, 4H), 6.948 (b, NH). $^{13}$C-NMR [CDCl$_3$]=25.68, 26.14, 29.19, 36.89, 39.20, 45.38, 58.60, 173.04. FTIR (cm$^{-1}$)=3303.67, 2921.83, 2852.83, 2811.75, 1635.01, 1538.76, 1468.29, 1379.05, 1238.83, 1100.88, 1041.46, 830.65, 714.41.

Synthesis of 4,4,16,16-tetramethyl-9,11-dioxo-4,8,12,16-tetraazanonadecane-4,16-diium-1,19-disulfonate (15.1)

The intermediate 13 (1.165 mmol) was taken in a clean and dried round bottom flask and dissolved in the 15 mL of ethyl acetate. Then, 1,3-propane sultone 14 (3.495 mmol) was added in reaction flask and the reaction was refluxed overnight. The precipitate formed during the reaction was filtered, washed with plenty of ethyl acetate and diethyl ether and then dried in vacuum using rotavapor. $^1$H-NMR [D20]=1.155-1.252 (m, 8H), 1.442 (m, 4H), 1.867 (t, 4H), 2.067 (t, 4H), 2.109 (t, 4H), 2.822 (t, 4H), 2.970 (s, 12H), 3.136 (t, 4H), 3.204 (t, 4H), 3.347 (t, 4H). 13C-NMR [CDCl$_3$]=18.11, 22.23, 225.24, 35.87, 47.15, 50.70, 61.85, 62,18, 177.56. FTIR (cm$^{-1}$)=3303.34, 2927.54, 2844.68, 1669.76, 1555.30, 1486.92, 1479.07, 1156.97, 1024.45, 929.32, 794.55, 682.02.

Synthesis of 5,5,17,17-tetramethyl-10,12-dioxo-5,9,13,17-tetraazahenicosane-5,17-diium-1,21-disulfonate (15.2)

The same method as discuss above with regard to 15.1 was adopted for the synthesis of 15.2, except that 1,4-butane sultone was used instead of 1,3-propane sultone. $^1$H-NMR [D20]=1.166-1.252 (m, 8H), 1.448 (m, 4H), 1.671 (t, 4H), 1.784 (t, 4H), 1.858 (t, 4H), 2.114 (t, 4H), 2.179 (t, 4H), 2.834 (t, 4H), 2.942 (s, 12H), 3.136-3.23 (m, 12H). $^{13}$C-NMR [CDCl$_3$] =20.82, 21.07, 22.23, 25.29, 28.18, 35.73, 35.91, 43.59, 49.94, 50.74, 61.70, 63.42, 177.55. FTIR (cm$^{-1}$)=3300.66, 2919.72, 2854.78, 1666.74, 1550.05, 1496.05, 1469.57, 1176.17, 1038.42, 956.74, 795.33, 686.20.

Viscosification Experiments

The zwitterionic surfactant 10 was mixed with either the gemini surfactant 15.1 or the gemini surfactant 15.2 in a weight ratio of 1:1. Each surfactant mixture was then added to two different concentrations of CaCl$_2$ in distilled water. The CaCl$_2$ was used at concentrations of 20% (Examples 1 and 3) and 30% (Examples 2 and 4) by weight. Thereafter, 10 wt. % of the total surfactant mixture (5 wt. % SDAS 10 and 5 wt. % of gemini 15.1 or 15.2) was added to 90 wt. % of the 20 or 30% CaCl$_2$ solutions. The viscosity of the surfactant solutions was measured at 40° C. and at 90° C. under different shear rates. The results are provided in Tables 1 and 2.

TABLE 1

Viscosity results with 15.1

|  | Conc. of SDAS 10 | Conc. of Gemini 15.1 | CaCl$_2$ (20%) | CaCl$_2$ (30%) | Viscosity (cPs; 40° C.) | Viscosity (cPs; 90° C.) |
|---|---|---|---|---|---|---|
| Example 1 | 5% | 5% | 90% | — | 3.35 | 14.60 |
| Example 2 | 5% | 5% | — | 90% | 3.18 | 9.77 |

TABLE 2

Viscosity results with 15.2

|  | Conc. of SDAS 10 | Conc. of Gemini 15.2 | CaCl$_2$ (20%) | CaCl$_2$ (30%) | Viscosity (cPs; 40° C.) | Viscosity (cPs; 90° C.) |
|---|---|---|---|---|---|---|
| Example 3 | 5% | 5% | 90% | — | 10.99 | 37.60 |
| Example 4 | 5% | 5% | — | 90% | 7.45 | 31.96 |

As is shown above, under all conditions that were studied, the viscosity of the solution greatly increased upon heating to 90° C. Viscosity of the treatment fluid dropped to <10 cP after mixing with 10% by volume diesel at a temperature of 90° C.

The properties of Examples 1-4 indicate the suitability of gemini and zwitterionic surfactants for use in wellbore fluids. These surfactants provide low-viscosity aqueous solutions that increase in viscosity under downhole conditions. When the wellbore fluid contacts a produced hydrocarbon its viscosity may drastically reduce, enabling easy flowback of the fluid post treatment.

Although the preceding description has been described herein with reference to particular means, materials and embodiments, it is not intended to be limited to the particulars disclosed herein; rather, it extends to all functionally equivalent structures, methods and uses, such as are within the scope of the appended claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed is:

1. A wellbore fluid, comprising:
   a gemini surfactant having a structure represented by formula (I):

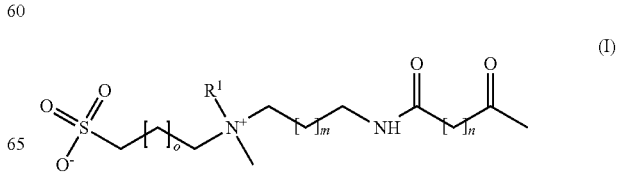

-continued

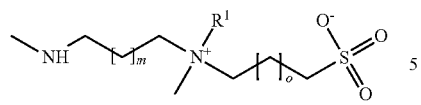

where $R^1$ is a $C_1$-$C_{10}$ hydrocarbon group, m and o are each, independently, an integer ranging from 1 to 4, and n is an integer ranging from 8 to 12;
a zwitterionic surfactant;
an activator; and
an aqueous base fluid.

2. The wellbore fluid according to claim 1, wherein the wellbore fluid contains the gemini surfactant in an amount of 1 to 15 wt. %.

3. The wellbore fluid according to claim 1, wherein the wellbore fluid contains the zwitterionic surfactant in an amount of 1 to 15 wt. %.

4. The wellbore fluid according to claim 1, wherein the wellbore fluid contains the activator in an amount of 10 to 30 wt. %.

5. The wellbore fluid according to claim 1, wherein the wellbore fluid further comprises an acid.

6. The wellbore fluid according to claim 1, wherein $R^1$ is a $C_1$ hydrocarbon group, o is 1 or 2, m is 1, and n is 8.

7. The wellbore fluid according to claim 1, wherein the zwitterionic surfactant has a structure represented by formula (II):

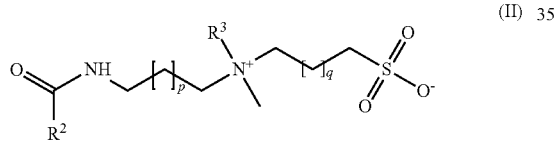

where $R^2$ is a $C_{15}$-$C_{27}$ hydrocarbon group or a $C_{15}$-$C_{29}$ substituted hydrocarbon group, $R^3$ is a $C_1$-$C_{10}$ hydrocarbon group, and p and q are each, independently, an integer ranging from 1 to 4.

8. A method for treating a hydrocarbon-containing formation, comprising:
injecting a wellbore fluid into a high permeability zone of a hydrocarbon-containing formation, wherein the high permeability zone increases the temperature of the wellbore fluid, resulting in the wellbore fluid having an increased viscosity;
wherein the wellbore fluid comprises:
a gemini surfactant having a structure represented by formula (I):

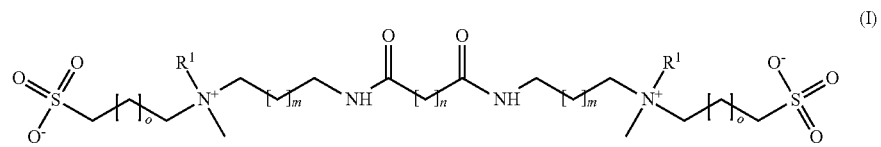

where $R^1$ is a $C_1$-$C_{10}$ hydrocarbon group, m and o are each, independently, an integer ranging from 1 to 4, and n is an integer ranging from 8 to 12;
a zwitterionic surfactant;
an activator; and
an aqueous base fluid.

9. The method according to claim 8, wherein the wellbore fluid contains the gemini surfactant in an amount of 1 to 15 wt. %.

10. The method according to claim 8, wherein the wellbore fluid contains the zwitterionic surfactant in an amount of 1 to 15 wt. %.

11. The method according to claim 8, wherein the wellbore fluid contains the activator in an amount of 10 to 30 wt. %.

12. The method according to claim 8, wherein the wellbore fluid further comprises an acid.

13. The method according to claim 8, wherein $R^1$ is a $C_1$ hydrocarbon group, o is 1 or 2, m is 1, and n is 8.

14. The method according to claim 8, wherein the zwitterionic surfactant has a structure represented by formula (II):

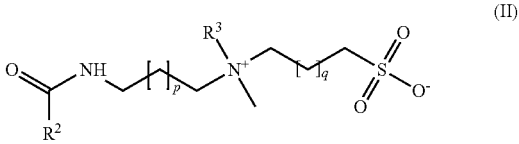

where $R^2$ is a $C_{15}$-$C_{27}$ hydrocarbon group or a $C_{15}$-$C_{29}$ substituted hydrocarbon group, $R^3$ is a $C_1$-$C_{10}$ hydrocarbon group, and p and q are each, independently, an integer ranging from 1 to 4.

15. A method for stimulating the recovery of hydrocarbons from a hydrocarbon-containing formation, the method comprising:
injecting a wellbore fluid into a high permeability zone of a hydrocarbon-containing formation, wherein the high permeability zone increases the temperature of the wellbore fluid, resulting in the wellbore fluid having an increased viscosity;

stimulating the hydrocarbon-containing formation using the wellbore fluid thereby creating pathways for hydrocarbon production; and recovering the hydrocarbons, wherein the wellbore fluid comprises:

a gemini surfactant having a structure represented by formula (I):

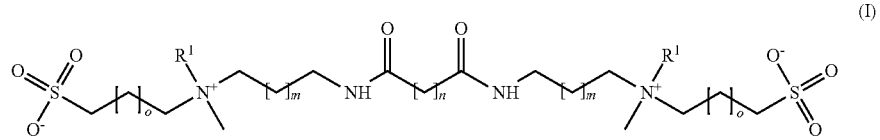

(I)

where $R^1$ is a $C_1$-$C_{10}$ hydrocarbon group, m and o are each, independently, an integer ranging from 1 to 4, and n is an integer ranging from 8 to 12;

a zwitterionic surfactant;

an activator; and an aqueous base fluid.

16. The method according to claim 15, wherein the wellbore fluid contains the gemini surfactant in an amount of 1 to 15 wt. %.

17. The method according to claim 15, wherein the wellbore fluid contains the zwitterionic surfactant in an amount of 1 to 15 wt. %.

18. The method according to claim 15, wherein the wellbore fluid contains the activator in an amount of 10 to 30 wt. %.

19. The method according to claim 15, wherein the wellbore fluid further comprises an acid.

20. The method according to claim 15, wherein $R^1$ is a $C_1$ hydrocarbon group, o is 1 or 2, m is 1, and n is 8.

21. The method according to claim 15, wherein the zwitterionic surfactant has a structure represented by formula (II):

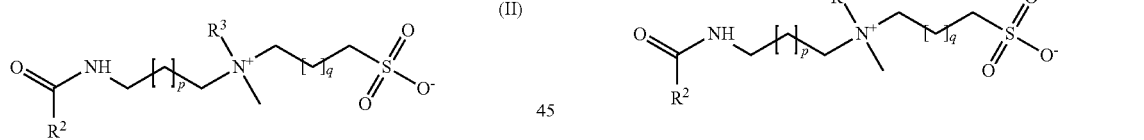

(II)

where $R^2$ is a $C_{15}$-$C_{27}$ hydrocarbon group or a $C_{15}$-$C_{29}$ substituted hydrocarbon group, $R^3$ is a $C_1$-$C_{10}$ hydrocarbon group, and p and q are each, independently, an integer ranging from 1 to 4.

22. A method of preparing a wellbore fluid, comprising:

mixing a gemini surfactant, a zwitterionic surfactant, an activator, and an aqueous base fluid, wherein the gemini surfactant has a structure represented by formula (I):

where $R^1$ is a $C_1$-$C_{10}$ hydrocarbon group, m and o are each, independently, an integer ranging from 1 to 4, and n is an integer ranging from 8 to 12.

23. The method according to claim 22, wherein the wellbore fluid contains the gemini surfactant in an amount of 1 to 15 wt. %.

24. The method according to claim 22, wherein the wellbore fluid contains the zwitterionic surfactant in an amount of 1 to 15 wt. %.

25. The method according to claim 22, wherein the wellbore fluid contains the activator in an amount of 10 to 30 wt. %.

26. The method according to claim 22 wherein the method further comprises mixing an acid with the gemini surfactant, the zwitterionic surfactant, the activator, and the aqueous base fluid.

27. The method according to claim 22, wherein $R^1$ is a $C_1$ hydrocarbon group, o is 1 or 2, m is 1, and n is 8.

28. The method according to claim 22, wherein the zwitterionic surfactant has a structure represented by formula (II):

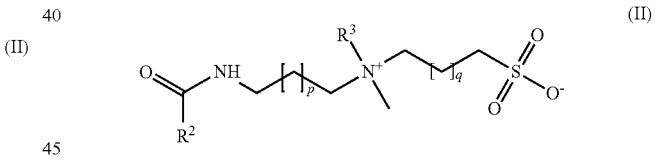

(II)

where $R^2$ is a $C_{15}$-$C_{27}$ hydrocarbon group or a $C_{15}$-$C_{29}$ substituted hydrocarbon group, $R^3$ is a $C_1$-$C_{10}$ hydrocarbon group, and p and q are each, independently, an integer ranging from 1 to 4.

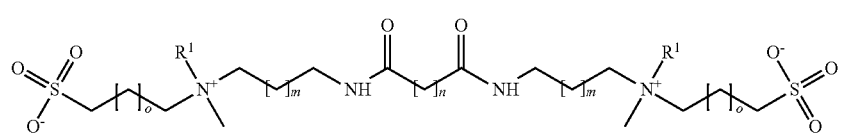

(I)

29. A gemini surfactant having a structure as represented by formula (I):
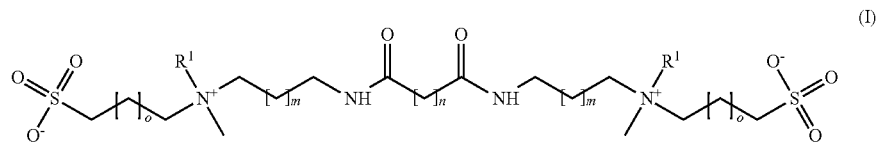
where $R^1$ is a $C_1$-$C_{10}$ hydrocarbon group, m and o are each, independently, an integer ranging from 1 to 4, and n is an integer ranging from 8 to 12.
30. The surfactant according to claim 29, wherein $R^1$ is a $C_1$ hydrocarbon group, o is 1 or 2, m is 1, and n is 8.
* * * * *